(12) United States Patent
Warnock

(10) Patent No.: US 7,698,763 B2
(45) Date of Patent: Apr. 20, 2010

(54) METHOD FOR CORRECTING DEFORMATIONAL PLAGIOCEPHALY AND OTHER CRANIAL DEFORMATIONS

(76) Inventor: Steven Warnock, 9829 S. 1300 East, Suite 200, Salt Lake City, UT (US) 84094

( * ) Notice: Subject to any disclaimer, the term of this patent is extended or adjusted under 35 U.S.C. 154(b) by 166 days.

(21) Appl. No.: 11/739,821

(22) Filed: Apr. 25, 2007

(65) Prior Publication Data
US 2007/0256242 A1 Nov. 8, 2007

Related U.S. Application Data

(60) Provisional application No. 60/797,758, filed on May 4, 2006.

(51) Int. Cl.
*A61G 15/00* (2006.01)
*A61F 5/00* (2006.01)

(52) U.S. Cl. .............................. 5/655; 5/636; 128/845; 602/17

(58) Field of Classification Search ............. 5/636–638, 5/655; 128/845; 602/17
See application file for complete search history.

(56) References Cited

U.S. PATENT DOCUMENTS

| | | | |
|---|---|---|---|
| 3,848,281 A * | 11/1974 | Mathews | 5/636 |
| 4,236,264 A | 12/1980 | Britzman | |
| 4,726,085 A | 2/1988 | Antonio | |
| D322,380 S | 12/1991 | El-Asir | |
| 5,177,823 A * | 1/1993 | Riach | 5/636 |
| 5,339,472 A | 8/1994 | Yin | |
| 5,546,619 A * | 8/1996 | Braun | 5/638 |
| 5,768,725 A | 6/1998 | Brenn | |
| D416,745 S | 11/1999 | Noyes | |
| 6,006,381 A | 12/1999 | Tandrup | |
| D420,845 S | 2/2000 | Rumage | |
| 6,052,849 A | 4/2000 | Dixon et al. | |
| 6,052,850 A | 4/2000 | Salido et al. | |
| 6,230,348 B1 | 5/2001 | Patrikakis | |
| D450,517 S | 11/2001 | Darling et al. | |
| 6,321,403 B1 | 11/2001 | Matthews | |
| 6,460,207 B1 | 10/2002 | Papay et al. | |
| 6,499,165 B1 | 12/2002 | Morgillo | |
| 6,536,058 B1 * | 3/2003 | Chang | 5/636 |
| 6,829,794 B2 | 12/2004 | Lenyo | |
| D501,349 S | 2/2005 | Harris et al. | |
| 2001/0008214 A1 | 7/2001 | Matthews | |
| 2003/0041380 A1 | 3/2003 | Hanley et al. | |
| 2005/0210592 A1 | 9/2005 | Littlehorn et al. | |
| 2008/0060134 A1 * | 3/2008 | Virga | 5/640 |

* cited by examiner

*Primary Examiner*—Michael Trettel
(74) *Attorney, Agent, or Firm*—Bateman IP Law Group

(57) ABSTRACT

A pillow is provided for the treatment of deformational plagiocephaly. The pillow preferably has arms which define a void with varying diameters to facilitate holding an infant's head to cause reshaping of the posterior of the skull. An anchoring mechanism may also be included to hold the pillow in place.

10 Claims, 5 Drawing Sheets

METHOD FOR CORRECTING DEFORMATIONAL PLAGIOCEPHALY AND OTHER CRANIAL DEFORMATIONS

BACKGROUND OF THE INVENTION

1. The Field of the Invention

The present invention relates to a device for treating deformational plagiocephaly. More particularly, the present invention relates to a device and method for correcting cranial deformation in a young child through minimally invasive means.

2. State of the Art

Over the last two decades, there has been a growing consensus among medical professionals that it is best to place an infant on his/her back while resting or sleeping. Some doctors and researchers have suggested that laying a child on his/her face increases the risk of Sudden Infant Death Syndrome (SIDS).

Because of this, it is much more common for an infant to be laid on his/her back for a substantial amount of time. For example, a child is placed on his/her back to sleep, as well as to entertain himself/herself while parents are otherwise occupied. Thus, an infant may spend as much as 20 plus hours per day laying on his/her back.

Because very young infants have relatively weak neck muscles and proportionately large heads, most young infants do not have the strength to move their heads from side to side. Thus, a young infant's head may remain tilted to one side or the other while the infant is lying on their back. At the same time, the bones in the infant's head are relatively soft and malleable. Thus, over a prolonged period of time, the weight of a child's head can gradually cause a deformation in the back of the skull called deformational plagiocephaly (i.e. a misshapen head). In this condition, a child will generally have a flattened spot on one side of their head as the soft bones conform to the flat surface of the bed, car seat, etc., while the weight of the head causes the skull to extend unevenly on the side on which the child is not resting. Over time, this can result in a pronounced protrusion on one side of the child's head accompanied by a relatively large flat spot on the other side of the head. While it is common for most children to have some asymmetry about their heads, the asymmetry caused by the protrusion and flattened portion can become quite pronounced and leave a clearly asymmetrical head. Once a deformation has occurred, the child is more likely to lay with the flattened portion of the skull on the mattress, etc., as it takes effort on the part of the child to rotate the head to position the protrusion at the bottom.

As a child reaches about 6 months old, the bones in the head begin to harden and permanently attach along the sutures and fontanelles. Thus, the shape of the head after 6 months of age remains more constant. If a child has deformational plagiocephaly at that time, the bones in the head will begin to harden in that shape. Thereafter to correct shape of the head usually requires the wearing of a helmet which applies pressure to the cranial bones as the child continues to grow, thereby ultimately achieving a more desired shape.

For young infants, however, deformational plagiocephaly is relatively easy to treat in accordance with the present invention when it is caused by positioning of the head. (Other forms of cranial deformation, may also be treatable by this method. However, for ease of convenience, the discussion will focus only on deformational plagiocephaly caused by sleep/rest position.)

Because the bones are still relatively malleable, selective control of the positioning of the head while a child sleeps provides for a natural, pain-free correction to the cranial deformation and provides a more symmetrical head shape. Thus, there is a need for a simple and inexpensive approach to correct deformational plagiocephaly. Additionally, it is desirable to provide such an approach which will cause little if any discomfort to the child and which does not require the wearing of the helmet and the like.

SUMMARY OF THE INVENTION

It is an object of the present invention to provide an improved method for treating cranial deformation in young children.

It is another and independent object of the present invention to create a device for facilitating reformation of head shape with minimal discomfort to the infant.

The above and other objects of the invention are accomplished in an apparatus method for reforming the head shape in an infant. In particular, the apparatus comprises a pillow which is configured to engage a child's head so as to maintain the head in substantially one position while the child rests. In a presently preferred embodiment, the pillow is generally horseshoe-shaped with a height and width size configured to facilitate placement around the child's head and to hold the head in a desired position.

In accordance with the present invention, a support pillow is provided which holds the child's head in substantially one position. The pillow preferably has a center diameter toward the top and a descending distance between the arms as one approaches the bottom.

In one desired embodiment, the support pillow is made of a foam or other firm but relatively soft material. The foam is sufficiently soft to avoid discomfort to the child's head, but sufficiently firm to hold the head in a desired position. In accordance with another aspect of the invention, the pillow may be covered with a soft material, such as terry cloth to avoid aggravation to the child's scalp.

In accordance with another aspect of the invention, a plurality of anchors or fasteners are disposed on the pillow to help the pillow remain in place on a mattress on which the child is sleeping or resting. For example, VELCRO, or other hook and loop fastener can be used to prevent the pillow from sliding due to the weight of the child's head leaning against one side of the pillow.

In accordance with the method, the child's head is positioned so that the protrusion in the child's head is placed against the flat or other surface on which the child is lying—typically a mattress—and the pillow is mounted around the head so as to keep the head in substantially that position. The positioning of the pillow can be adjusted so that it supports the head on both sides of the protrusion so that the head will not follow the natural tendency to roll to either side of the protrusion.

Over a prolonged period of time, the pressure of the head against the bed, car seat, etc., will gradually flatten the protrusion in the back of the child's head much in the same way the original flattened spot was formed. As the protrusion is being flattened, the natural area of expansion for the cranial bones is the previously formed flattened spot. Thus, as the protrusion is flattened/rounded, the flat spot is extended and rounded thereby providing a more symmetrical head shape.

When used with a young child, the deformation in the cranium can be fixed within a few days to a few weeks depending on severity while the bones are still soft and malleable. There is little, if any, discomfort to the infant and by adjusting position of the head as it is held by a pillow, a parent or health care provider can eliminate a more substantially pronounced cranial deformation.

DETAILED DESCRIPTION

The present invention will now be discussed in respect to the drawings so as to enable one of ordinary skill in the art to make or use the invention. It will be appreciated that the drawings and descriptions are exemplary only and are not intended to limit the scope of the invention set forth in the appended claims. Furthermore, it will be appreciated that various aspects of the invention may be discussed with respect to some embodiments shown and not with respect to others in the interest of brevity and it should be understood that any aspect of the invention discussed with respect to one figure may, in accordance with the present invention, be included with other figures.

Figure 1:
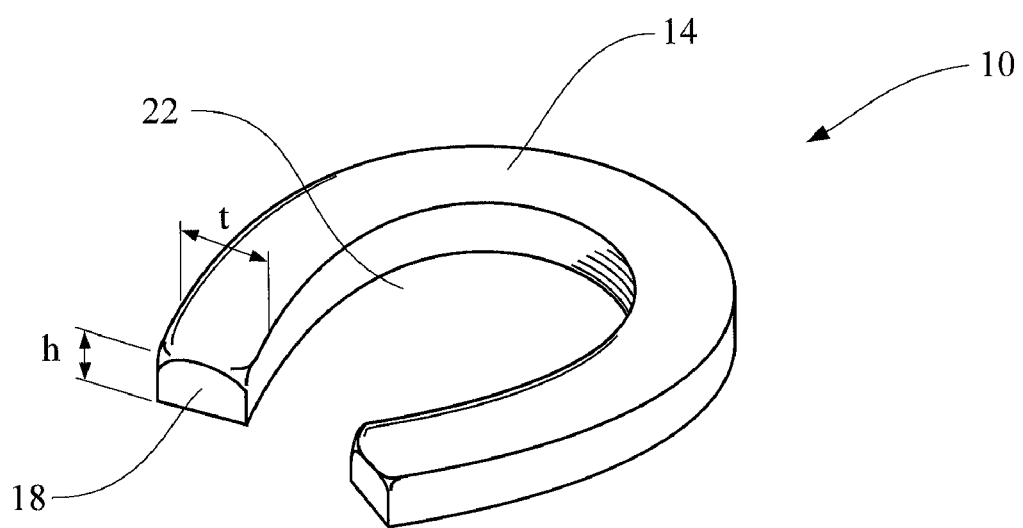
FIG. 1 shows a perspective view of a pillow formed in accordance with the principles of the present invention.

Turning now to FIG. 1, there is shown a perspective view of a pillow, generally indicated at 10, formed in accordance with the principles of the present invention. The pillow comprises an arcuate upper portion 14 and an open lower portion 18 so as to be generally horse shoe shaped with a center void 22. Other shapes may be used, such as rounding off the opening with a member which is sufficiently shallow to fit under a child's neck.

Preferably, the pillow 10 has a generally consistent height (h) and thickness (t). As will be discussed in additional detail below, the consistent height h and thickness t facilitate rotation of the pillow in a variety of directions to comfortably engage an infant's head and hold the head in a desired position.

The pillow 10 is preferably a height which is sufficiently tall to support an infant's head to prevent it from rolling from side to side. At the same time, however, the pillow 10 is preferably low enough that it is not overly cumbersome or confining. Currently, it is believed that a height between 0.75 and 2.0 inches is preferred. Likewise, a thickness of between 0.75 and 2.0 inches is presently preferred.

Figure 2:
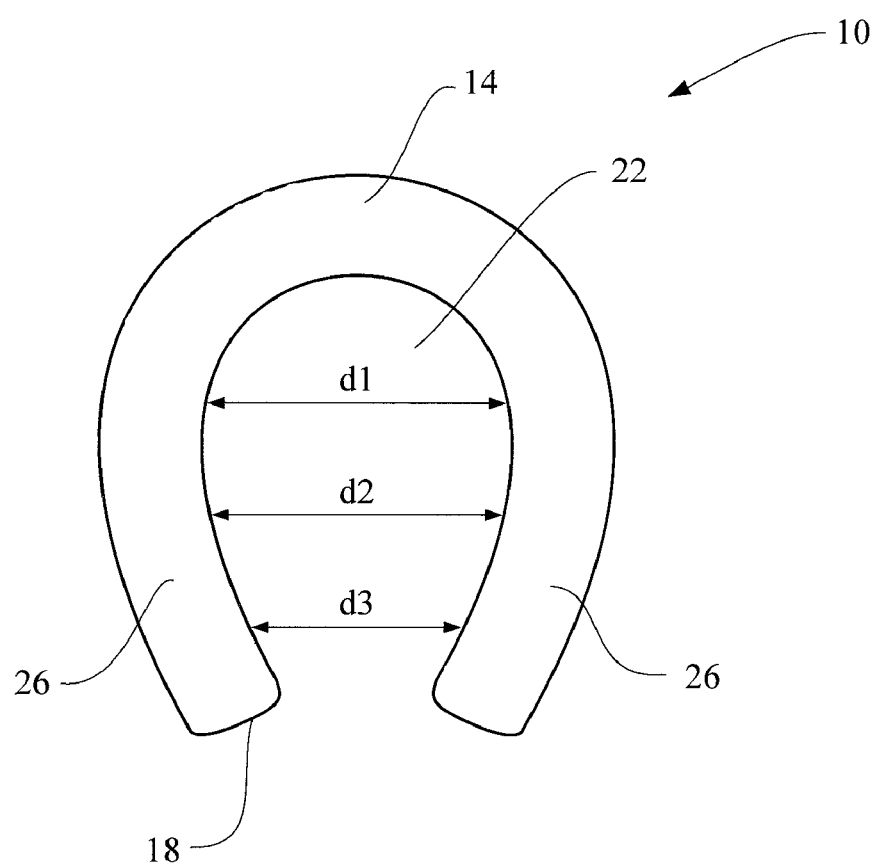
FIG. 2 shows a plan view of a pillow formed in accordance with the principles of the present invention.

Turning now to FIG. 2, there is shown a plan view of the pillow 10. The arms 26 of the pillow gradually curve toward each other. This provides the void 22 with a varying diameter, represented by d1, d2 and d3. It will be appreciated that there is considerable difference in the size of infants' heads. In order to provide a pillow 10 that can be used over the first six months of a child's life, a varying diameter is provided in the void. As the child gets older, or when using with a child with a large head, the head will be positioned higher in the void 22 represented by d1, whereas a newborn or premature infant may have the head centered more closely to the lower end as represented by d3. Thus, a parent or other caregiver is able position the pillow relative to the child's head to obtain a position which is both comfortable to the child and which will hold the child's head in the desired position while the deformation is corrected.

Figure 3:
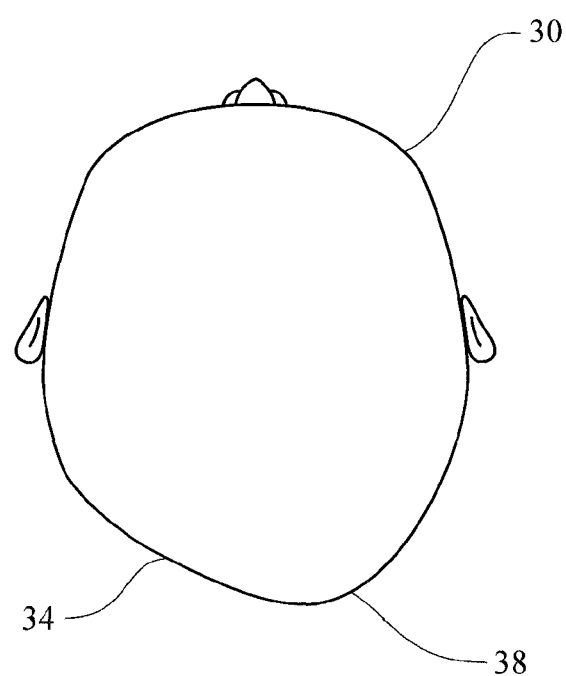
FIG. 3 shows a top view of an infant's head wherein the infant is suffering from deformational plagiocephaly.

Turning now to FIG. 3, there is shown a top view of an infant's head 30 wherein the infant is suffering from deformational plagiocephaly. Because the infant has spent extensive periods of time lying on the left side of the head 30, a flattened spot or area 34 has developed on the left side. As the left side has flattened, this has caused a protrusion 38 to develop on the right side. If left untreated, the cranial deformation can become permanent, leaving the child with a misshapen head. While such conditions are often treated by having a child wear a helmet to gradually reshape the bone, it can be resolved much more rapidly and conveniently in accordance with the present invention.

Figure 4:
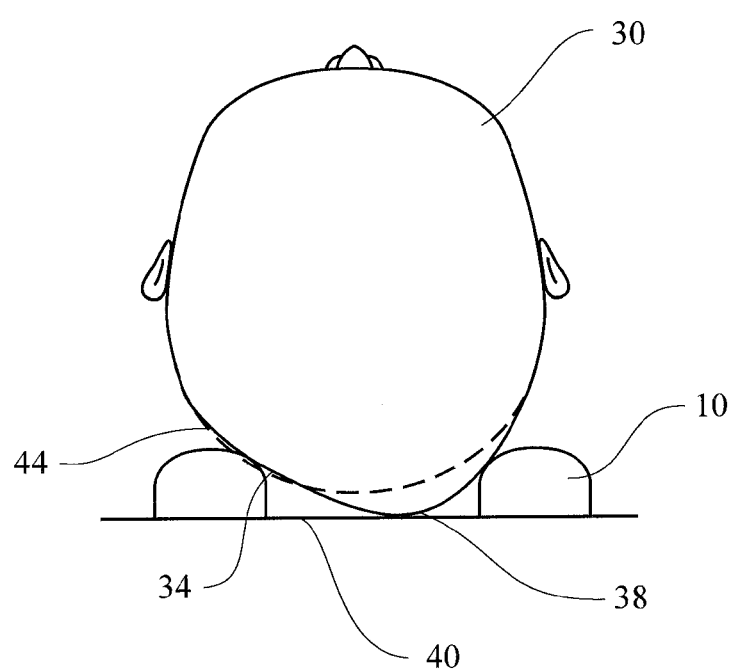
FIG. 4 shows a top view of an infant's head being held in a desired position by the pillow of FIG. 1.

Turning now to FIG. 4, there is shown the infant's head 30 resting in the pillow 10. The pillow 10 is placed on a bed 40, in a car seat or on some other surface where the infant's head would typically be positioned for a prolonged period of time. The head 30 is positioned in the pillow 10 so that the protrusion 38 rests on the bed 40, etc. As the protrusion 38 rests on the bed, the weight of the head will gradually push on the protrusion and cause it to flatten (in the same manner the flattened spot 34 was formed). As the protrusion flattens, it will cause other parts of the skull to protrude in compensation. As shown by dashed line 44, this will most commonly occur along the flattened area 34, rounding the posterior of the skull. Depending on the severity of the protrusion 38 and the flexibility of the bone, this can take from as little as a couple of days to a number of weeks. However, it is far more convenient and less burdensome to the child than wearing a helmet later to reshape the head.

Figure 5:
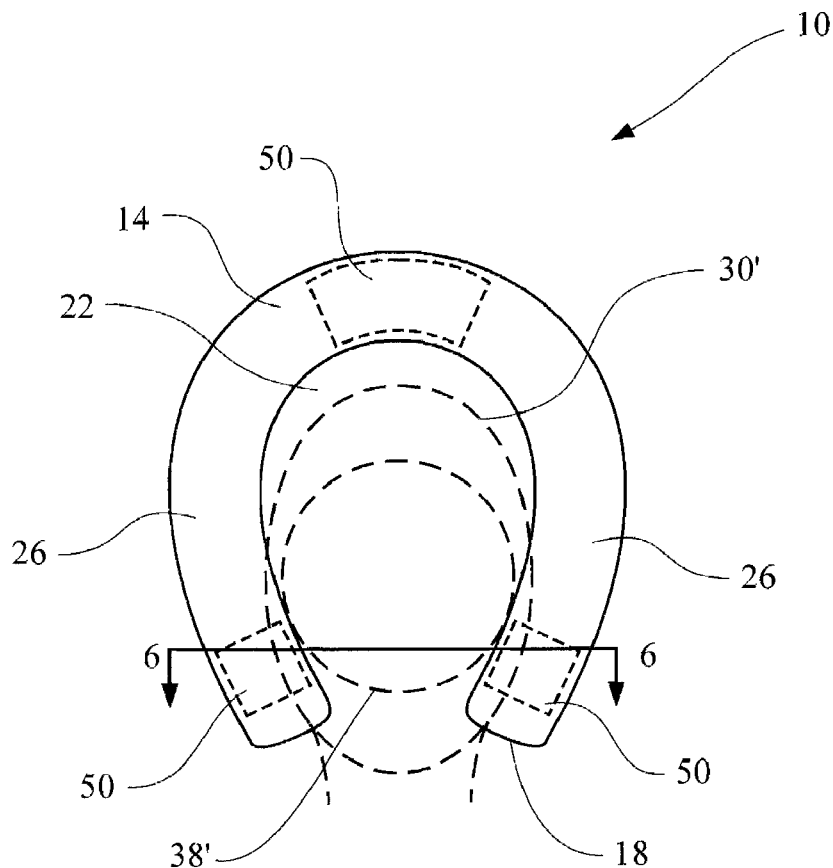
FIG. 5 shows a plan view of the pillow of FIGS. 1 and 2, with dashed lines representing the positioning of an infant's head resting in the pillow to correct deformational plagiocephaly, and other dashed lines demonstrating an anchoring system for maintaining the pillow in a desired position.

Turning now to FIG. 5, there is shown the pillow 10. An infant's head is represented by the dashed lines 30' and the area of the head containing the protrusion is shown by dashed line 38'. Because the arms 26 of the pillow 10 provide a void 22 of varying diameter, a parent or other caregiver can adjust the location of the pillow so that the arms engage the head 30' in the right location to hold the protrusion 38' against the bed, etc. For larger heads, the head can be moved more toward the upper end 14, and smaller heads, such as that shown in FIG. 5, can be moved toward the bottom end 18. If desired, the pillow 10 can also be rotated relative to the head to help obtain the desired head shape.

The time that it takes to reshape the head can depend on a variety of factors. For example, an infant with a significant protrusion may take 12 plus hours per day for many weeks. In contrast, an infant with a fairly modest protrusion may require a few days at twelve hours per day, or a week or two at some shorter interval. It is preferred, however, that an infant suffering deformational plagiocephaly use the device at least a majority of the time that his or her head will be resting on a bed, etc., and even more preferably at least 8 hours per day.

Those skilled in the art will appreciate that the pillow 10 can be made from a variety of different materials. Two preferred materials are open cell and closed cell foams. Such materials are relatively lightweight, durable, and unlikely to cause injury if grasped by the infant. It is preferable, however, that the bottom surface of the pillow be formed from a material which is relatively high friction. For example, the body can be formed of nearly any material and then covered with a high friction cover or coating. In the alternative, the entire pillow may be formed from foam, certain plastics, silicon, rubber or rubber-like material. These materials work well because they are high friction while providing very low abrasion qualities. The high friction aspect of the outer surface helps both to hold the pillow in place on the sheet and to prevent the infant's head from sliding relative to the pillow, while the low abrasion will prevent irritation to the infant's skin. The infant's head is held in the proper position to place pressure against the protrusion and reshape the head.

Also shown in FIG. 5 are a plurality of anchoring mechanisms 50. The anchoring mechanisms 50 can be used in place of an abrasive or high friction surface. A number of different anchoring mechanisms can be used. For example, a plurality of hook and loop fasteners (VELCRO) can be attached to the bottom of the pillow 10. The hook and loop fasteners 50 will engage the fabric on the bed, car seat, etc., and prevent the pillow from sliding side to side in response to the weight of the infant's head. This enables the rest of the pillow to be made from a softer material or to have a softer outer surface, as the resistance of the pillow to movement will help hold the head in place.

Figure 6:
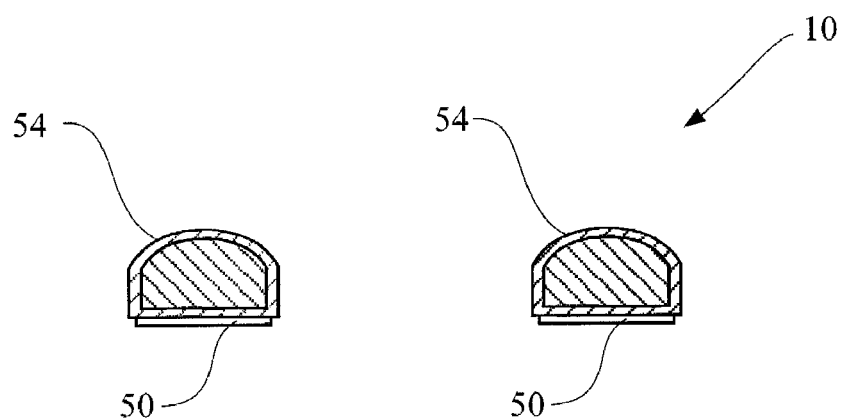
FIG. 6 shows a cross-sectional view of a pillow, which is covered by a cloth casing and which includes an anchoring mechanism for holding the pillow in place during use.

Turning now to FIG. 6, there is shown a cross-sectional view of the pillow 10 taken along the line 6-6. In addition to the anchoring mechanism 50, which can be hook and loop fastener, adhesive fasteners, buttons, etc., the pillow 10 includes a cover 54. The cover 54 may be made from a variety of materials, such as cotton, flannel, or other materials which are generally soft and will provide minimal irritation with prolonged contact with the infant's head. Thus, for example, the cover 54 may be made from terry cloth.

The cover 54 may be sewn onto the pillow 10, with the entire pillow being washable. In the alternative, the cover 54 may include an opening to allow the pillow to be removed so that the cover may be washed periodically to remove the buildup of skin oils, spilled formula, etc. Thus, the pillow may be used for a prolonged period of time, and even with multiple children. When the cover 54 gets soiled, it can be removed, cleaned, and returned to the pillow. It will also be appreciated that the cover 54 could extend between opposing sides of the pillow, so that the infant's head actually rests on a portion of the cover resting on the mattress, etc. As used herein, reference to placing the infant's head on a surface may include a mattress or such a cover.

Thus there is disclosed an apparatus and method for treating deformational plagiocephaly and other cranial deformations. Those skilled in the art will appreciate that numerous modifications can be made without departing from the scope and spirit of the invention. The appended claims are intended to cover such modifications.

What is claimed is:

1. A method for treating deformational plagiocephaly, the method comprising:
   selecting a pillow having a void formed therein;
   selecting an infant having deformational plagiocephaly wherein a head of the infant has a protrusion; and
   positioning the pillow on a surface and placing the head in the pillow so as to keep the protrusion in contact with the surface.

2. The method according to claim 1, wherein the method comprises selecting a pillow having a void with a varying diameter and adjusting the position of the pillow relative to the infant's head.

3. The method according to claim 1, wherein the method comprises selecting a pillow of a generally consistent height and width.

4. The method according to claim 1, wherein the method comprises using the pillow to support the infant's head at least 8 hours per day until the protrusion decreases a desired amount.

5. The method according to claim 1, wherein the method comprises adjusting the pillow to gradually reshape the infant's head.

6. The method according to claim 1, wherein the method comprises anchoring the pillow to the surface.

7. The method according to claim 1, wherein the method comprises covering the pillow with a cover to minimize irritation to an infant's scalp.

8. A method for reducing a cranial protrusion in an infant's head, the method comprising:
   disposing the infant's head so that the cranial protrusion is disposed against a generally flat surface, and
   disposing a pillow adjacent the infant's head so that the pillow engages opposing sides of the head and holds the protrusion against the generally flat surface.

9. The method of claim 8, wherein the method comprises utilizing a pillow which is generally horseshoe shaped.

10. The method of claim 8, wherein the method comprises anchoring the pillow to a generally flat surface.

* * * * *